United States Patent
Gelbman et al.

(10) Patent No.: US 9,494,609 B2
(45) Date of Patent: Nov. 15, 2016

(54) STATUS DISPLAYING SAMPLE CARRIERS

(71) Applicants: Alexander Gelbman, Florham Park, NJ (US); Benjamin Samuel Pollack, Budd Lake, NJ (US)

(72) Inventors: Alexander Gelbman, Florham Park, NJ (US); Benjamin Samuel Pollack, Budd Lake, NJ (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 14/376,120

(22) PCT Filed: Feb. 1, 2013

(86) PCT No.: PCT/US2013/024371
§ 371 (c)(1),
(2) Date: Jul. 31, 2014

(87) PCT Pub. No.: WO2013/116669
PCT Pub. Date: Aug. 8, 2013

(65) Prior Publication Data
US 2014/0370608 A1 Dec. 18, 2014

Related U.S. Application Data

(60) Provisional application No. 61/594,498, filed on Feb. 3, 2012.

(51) Int. Cl.
*G01N 35/02* (2006.01)
*G01N 35/00* (2006.01)
(Continued)

(52) U.S. Cl.
CPC ......... *G01N 35/00584* (2013.01); *B01L 3/545* (2013.01); *G01N 35/0095* (2013.01); *G01N 35/00732* (2013.01); *G06F 3/147* (2013.01); *B01L 2300/022* (2013.01); *B01L 2300/023* (2013.01); *B01L 2300/024* (2013.01); *B01L 2300/027* (2013.01);
(Continued)

(58) Field of Classification Search
CPC ............... Y10T 436/00; Y10T 436/11; Y10T 436/113332; G01N 35/00584; G01N 35/00; G01N 35/0095; G01N 35/0092; G01N 35/00732; G01N 35/00722
USPC .......................... 436/47, 43; 422/67, 63, 500
See application file for complete search history.

(56) References Cited

U.S. PATENT DOCUMENTS

2002/0167500 A1  11/2002  Gelbman
2003/0132924 A1  7/2003  Hamilton
(Continued)

FOREIGN PATENT DOCUMENTS

DE   10 2006 041695 A1   3/2008

OTHER PUBLICATIONS

E Ink Triton™, E Ink Triton™Imaging Film, E Ink Corporation, Nov. 2010, data sheet obtained on Jan. 9, 2016.*
(Continued)

*Primary Examiner* — Christine T Mui

(57) ABSTRACT

An automation system for an in vitro diagnostics environment includes a plurality of intelligent carriers that include onboard processing and navigation capabilities. To aid in operator handling of payloads and carriers, carriers include an electronically rewritable display on a surface visible to an operator. The display can include an LCD, E-ink, or other rewritable display and can utilize color, pattern, or text to convey status information of the payloads to the operator.

38 Claims, 11 Drawing Sheets

(51) Int. Cl.
  *B01L 3/00* (2006.01)
  *G06F 3/147* (2006.01)
  *G01N 35/04* (2006.01)

(52) U.S. Cl.
  CPC .............. *G01N 2035/00306* (2013.01); *G01N 2035/00782* (2013.01); *G01N 2035/00801* (2013.01); *G01N 2035/00891* (2013.01); *G01N 2035/0406* (2013.01); *G01N 2035/0467* (2013.01); *G01N 2035/0477* (2013.01); *G09G 2340/14* (2013.01); *G09G 2380/04* (2013.01); *Y10T 436/113332* (2015.01)

(56) References Cited

U.S. PATENT DOCUMENTS

| | | |
|---|---|---|
| 2005/0159982 A1 | 7/2005 | Showalter et al. |
| 2005/0237203 A1 | 10/2005 | Burman et al. |
| 2008/0164210 A1 | 7/2008 | Demarco |
| 2008/0309551 A1 | 12/2008 | Gelbman |
| 2009/0210254 A1 | 8/2009 | Gurney |
| 2009/0295549 A1 | 12/2009 | Han |
| 2010/0129262 A1 | 5/2010 | Shanafelter |
| 2010/0227387 A1 | 9/2010 | Safar et al. |
| 2011/0226859 A1 | 9/2011 | Chen |
| 2012/0024943 A1 | 2/2012 | Kangas |

OTHER PUBLICATIONS

PCT International Search Report and Written Opinion dated Apr. 11, 2013 (10 Pages).
Extended EP Search Report dated Aug. 28, 2015 of corresponding European Patent Application No. 13743163.1, 3 Pages.

* cited by examiner

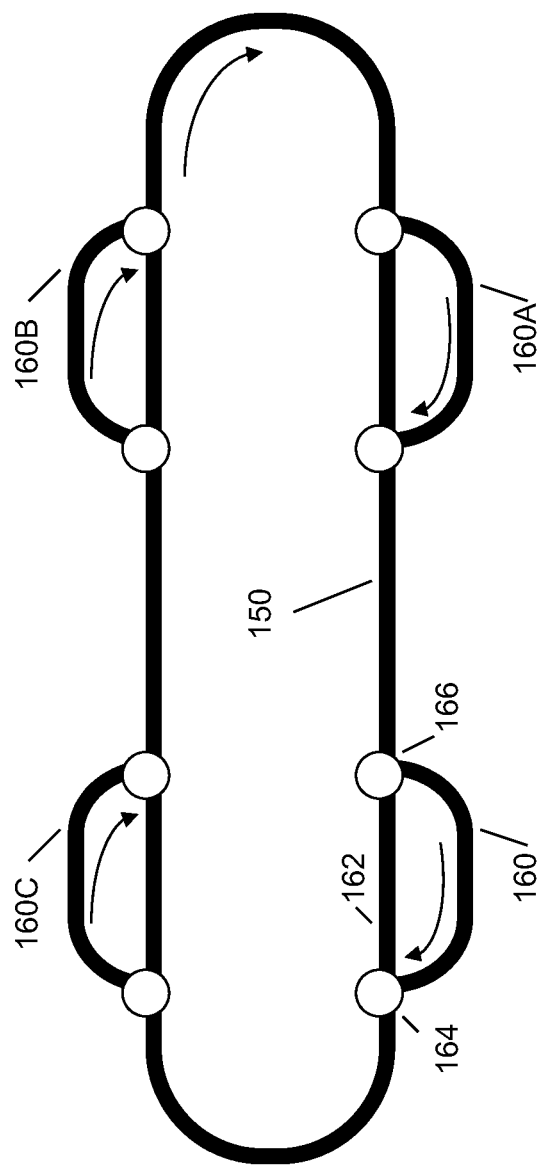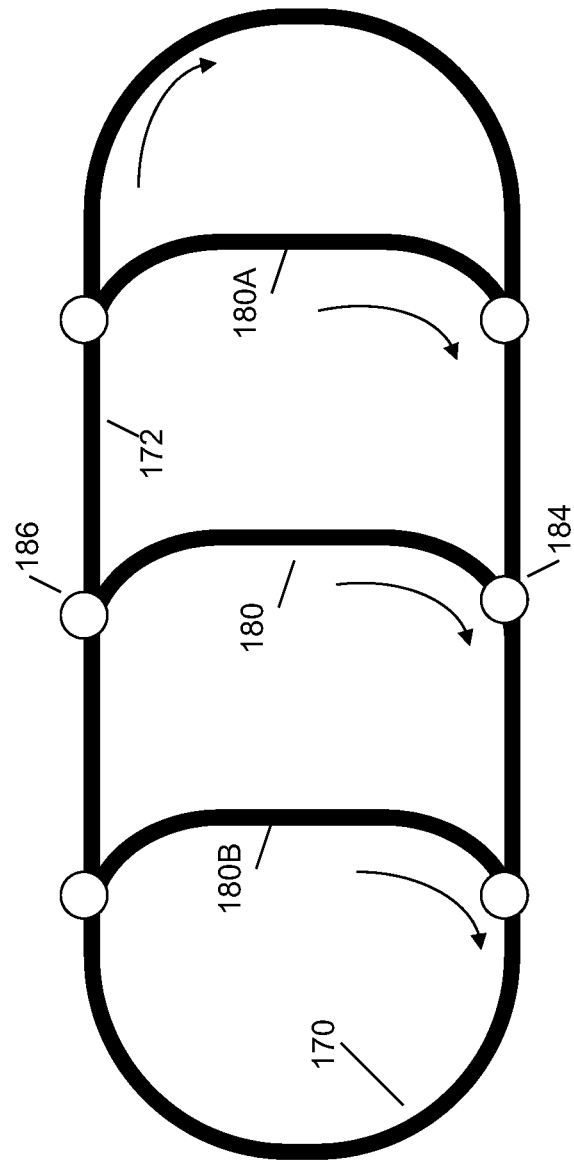

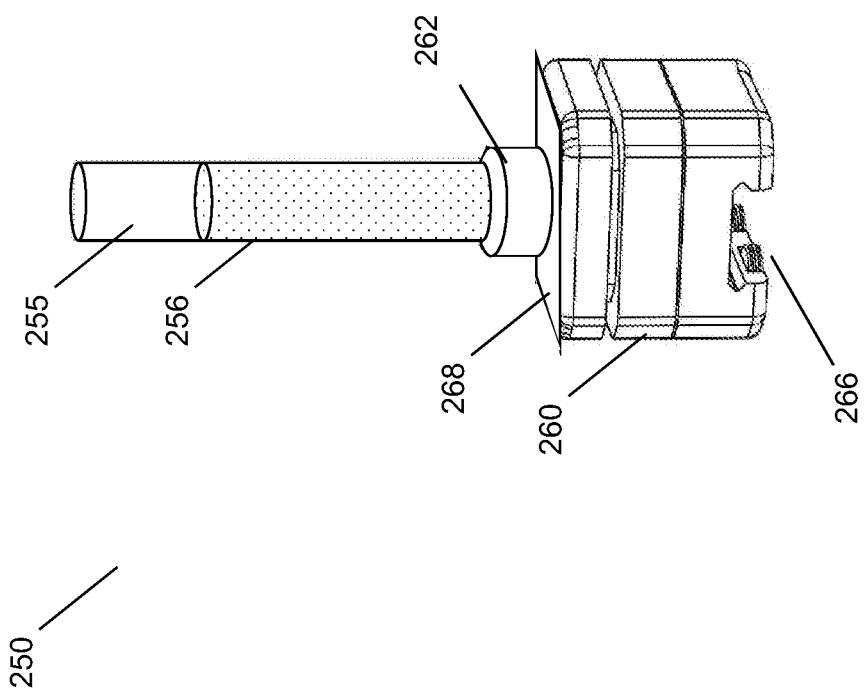

| A001 | N/A | A002 |
|---|---|---|
| 452 | 472 | 462 |
| Complete | Bad Barcode | Xfer To IA(5) |
| A003 | A006 | A005 |
| 464 | 474 | 454 |
| Xfer To IA(5) | Short Sample | Complete |
| A009 | A007 | A008 |
| 466 | 456 | 476 |
| Xfer To IA(9) | Complete | Clot |

FIG. 8

STATUS DISPLAYING SAMPLE CARRIERS

CROSS-REFERENCE TO RELATED APPLICATIONS

This application claims priority to U.S. provisional application Ser. No. 61/594,498 filed Feb. 3, 2012, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer via active transport devices. Embodiments of the present invention are particularly well suited, but in no way limited, to carriers for transporting fluid samples in an in vitro diagnostics environment, having a rewriteable electronic display for automatically displaying status information about a fluid sample.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths. A drawback with this set up is that singulation must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track. As a result, dozens or hundreds of pucks can be on the track of an automation system at one time, making it difficult or impossible for an operator to keep track of samples.

An operator of an analyzer must often handle samples by hand. For example, an operator might need to sort samples in a sample tray, move the samples to an analyzer, remove the samples from that analyzer, and transport samples to another analyzer. In the case of a handling error, an operator may need to remove samples from an automation system for visual inspection. Currently, there is no active way of conveying the status information of samples to an operator for his/her attention. Instead, an operator must typically use a handheld barcode scanner or printed sheet to reveal any status information about a sample. The status information is often stale and does not provide real-time or at-a-glance status information to an operator. Furthermore, IVD operators may lack training necessary to understand complicated status information and relying on an operator to hand scan or compare samples to a status sheet may introduce an element of human error into a testing environment. Accordingly, there is a need for a way of providing simple visual information about the status of samples in an IVD environment.

SUMMARY

Embodiments of the present invention address and overcome one or more of the above shortcomings and drawbacks, by providing devices and systems for visually displaying information about one or more payloads, such as one or more sample containers, on one or more surfaces of a rack or carrier that holds the sample. By displaying human recognizable information on a rack or carrier, a human operator can more easily manage a large number of samples and quickly determine information, such as status information about the sample. This technology is particularly well-suited for, but by no means limited to, racks and carriers for use in an automation system in an in vitro diagnostics (IVD) environment.

Embodiments of the present invention may be directed to carriers and racks having means to hold one or more samples and at least one electronically rewritable surface that can be updated by a processor or an outside controller to display information that may be relevant to an operator of an IVD laboratory system.

According to one embodiment of the invention, a carrier for use in an in vitro diagnostics environment includes a bracket for accepting one or more payloads. At least one surface has an electronically rewritable display. The carrier automatically updates the electronically rewritable display to provide a visual indication of status information regarding the one or more payloads. A payload may include, but may not be limited to, a sample vessel configured to hold a fluid patient sample.

According to another aspect of some embodiments, the status information can be updated wirelessly by a central controller. According to another aspect of some embodiments, the one or more payloads include one or more sample containers and the carrier automatically updates the electronically rewritable display to provide a visual indication of status information regarding the one or more sample containers.

According to another embodiment of the invention, a carrier for use in an in vitro diagnostics environment includes an electronically rewriteable display configured to display status information, a processor configured to update the electronically rewriteable display, and a wireless receiver configured to receive the status information for display. The status information relates to the status of one or more payloads being carried by the carrier.

According to another aspect of some embodiments, the electronically rewritable display is a bi-stable display. According to another aspect of some embodiments, the display can be updated by temporary application of power to electrical contacts on the carrier. According to another aspect of some embodiments, the electronically rewritable display is a non-volatile display. At least one aspect of some embodiments anticipates that status information is conveyed by displaying a color, a pattern (which may include blinking), text (which may include instructions for the handling of the sample), or any subset or combination thereof on at least a portion of the electronically rewritable display. According to yet another aspect of some embodiments, the status information indicates a priority of the one or more payloads, an identity of at least one patient sample among the one or more payloads, and/or a response to a query by an operator. According to still another aspect of some embodiments, a response can be conveyed such that at least a portion of the rewritable electronic display is made to appear different from a group of other carriers in response to the query.

According to another aspect of some embodiments, the rewritable electronic display comprises more than one region for displaying the status information. According to yet another aspect of some embodiments, the carrier includes one or more sensors for determining the presence of the one or more payloads.

According to another embodiment of the invention, a method for displaying status information of one or more payloads being transported in an in vitro diagnostics environment includes the steps of associating information pertaining to the one or more payloads with a carrier holding the one or more payloads, receiving, by the carrier, status information pertaining to the one or more payloads, and displaying the status information on an electronically rewritable surface of the carrier.

According to another aspect of some embodiments, the method also includes the step of updating the electronically rewritable display to reflect one or more changes in the status information of the one or more payloads. According to another aspect of some embodiments, one or more changes can include an error condition pertaining to the one or more payloads. According to another aspect of some embodiments, the step of associating information pertaining to the one or more payloads includes reading a barcode on the one or more payloads to determine an identity of the one or more payloads and changing the display of the carrier to distinguish the carrier from a group of carriers and to instruct the operator to place the one or more payloads into the carrier. According to yet another aspect of some embodiments, the method includes detecting the presence of a new payload in the carrier after the barcode has been read to determine that the new payload has been placed in the carrier. These aspects may be particularly suitable where the one or more payloads include patient samples. According to still another aspect of some embodiments, the method further includes the step of updating the electronically rewritable display to reflect the result of a query if the one or more payloads meet criteria of the query. Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

FIG. 8 is a diagrammatic view of multiple exemplary states of electronically rewritable surfaces for displaying status information about a samples arranged in an array.

DETAILED DESCRIPTION OF ILLUSTRATIVE EMBODIMENTS

Figure 1:
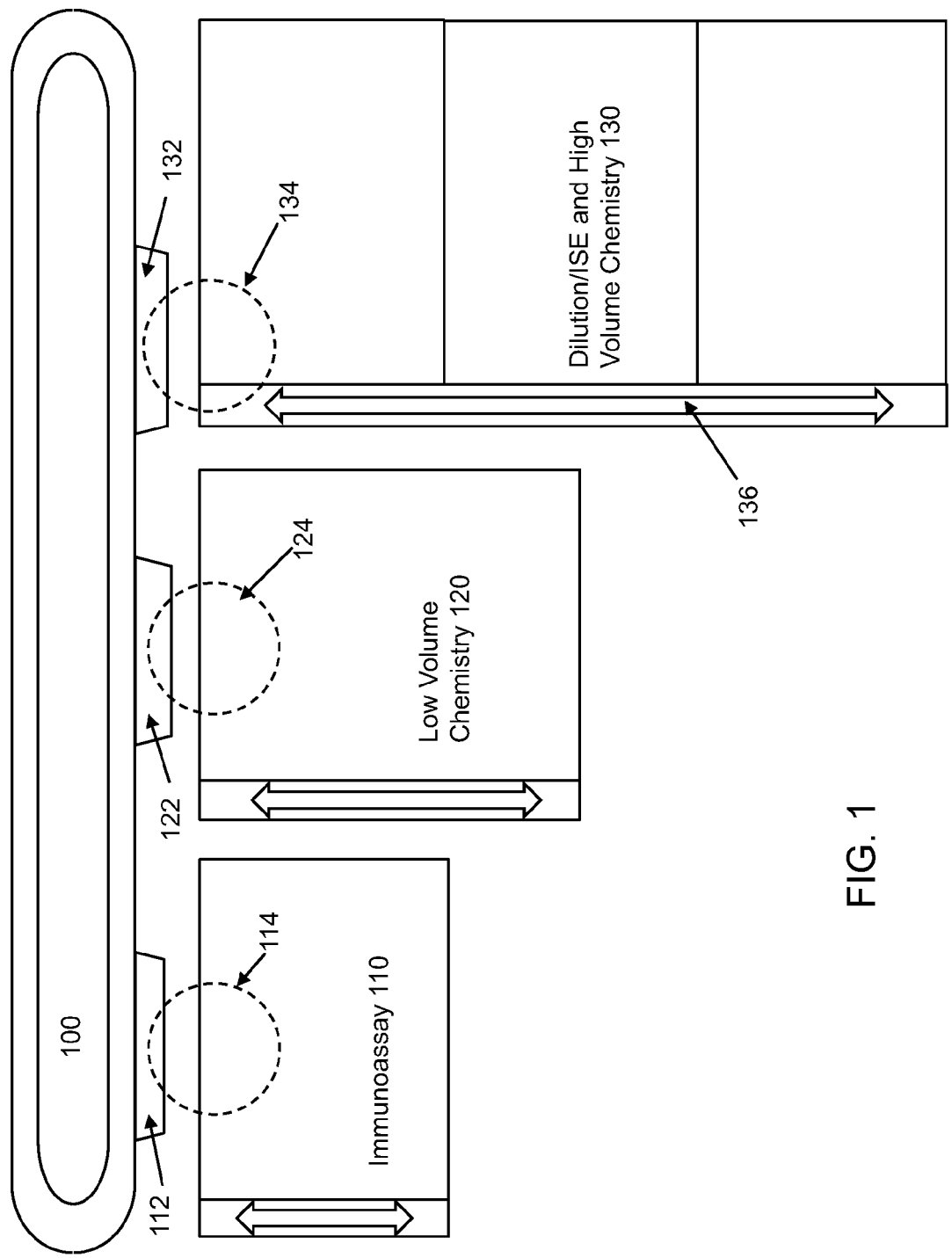
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

EXEMPLARY EMBODIMENTS

Embodiments include improved apparatuses and methods for reliably and/or automatically displaying status information about samples as the samples are being transported within an automated clinical analyzer (analyzer). Specifically, carriers within an automation system can include a rewritable surface for displaying status information automatically. By providing this information on an electronically rewritable surface, the status information can be readily displayed to an operator and updated in real time as the status of the sample changes as the sample moves within an in vitro diagnostics (IVD) environment.

In some embodiments, the carriers that transport fluid samples are active devices. These can include semi-autonomous carriers that include onboard power and memory. The memory can include, inter alia, the current status of the sample to be displayed, while the power can be used to update the rewritable surface to display that status.

In some embodiments, active carriers can transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options.

Embodiments of the present invention may include systems and methods that provide a more efficient lab automation system to allow samples to be shuttled between and amongst various analyzer testing stations with less latency and more individual control. Embodiments of the present invention may reduce or eliminate queues experienced by samples traversing the automation system. Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

In some embodiments, multiple analyzers can be used in the same IVD environment. For example, older analyzers, standalone analyzers, or analyzers that provide substantially different testing mechanisms can be on separate automation systems. An operator may carry trays of samples between and amongst these machines.

Modular Automation System for Use with Carriers

An exemplary track geometry, for use in transporting samples within an analyzer typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within the WD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
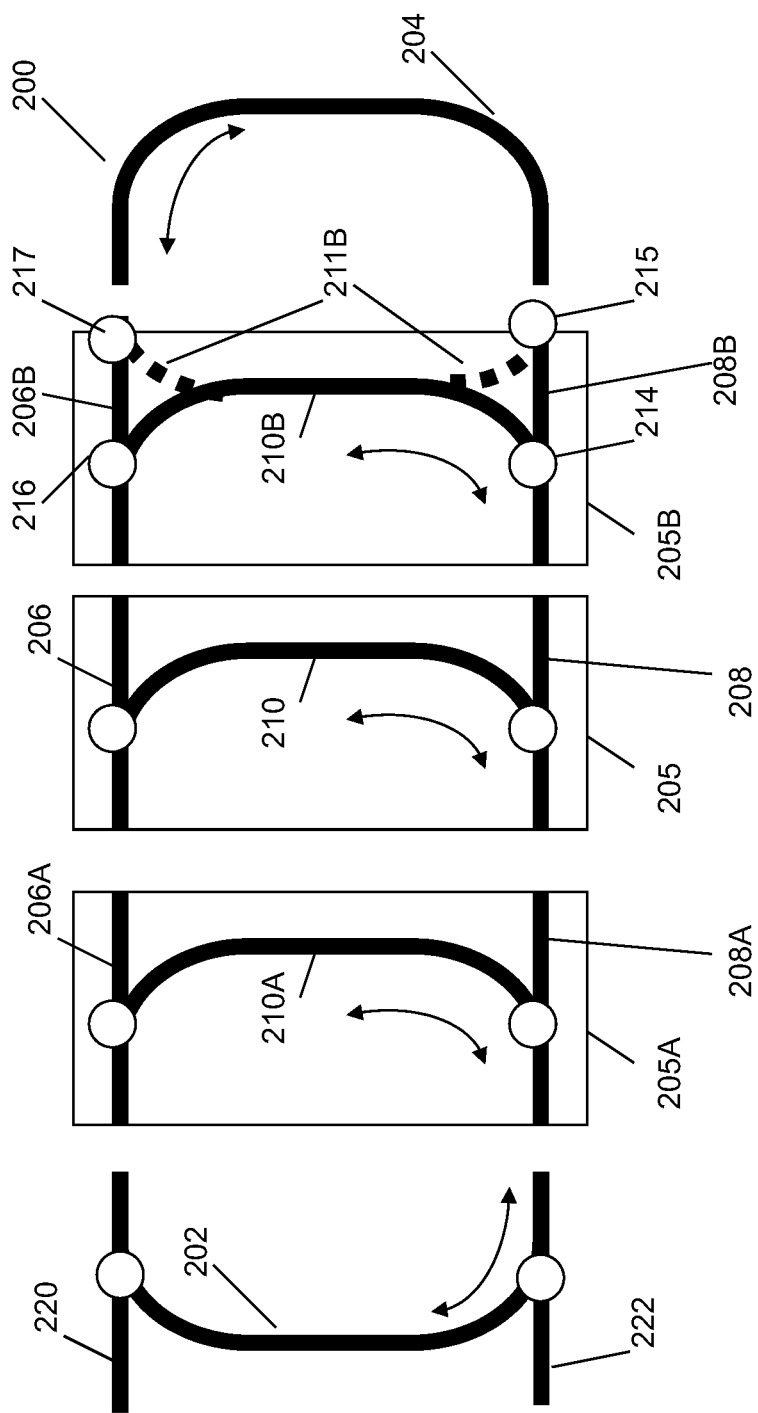
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges. Sample carrier 250 includes a main housing 260, which can house the internal electronic components describe herein. The main housing 260 supports a bracket 262, which can accept a payload. In some embodiments, this is a shallow hole that is designed to accept a sample tube 255 and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Housing 260 is supported by guide portion 266, which allows the carrier 250 to follow a track between decision points. Guide portion 266 can include, for example, a slot to accept one or more rails in the track, providing lateral vertical support. In some embodiments, the guide portion allows the carrier 250 to be guided by walls in the track, such as the walls of a trough shaped track. The guide portion 266 can also include drive mechanisms, such as friction wheels that allow a motor in the carrier housing 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. In some embodiments, carriers may hold more than one sample and rewritable displays may display status information about one or more samples in the carriers. In other embodiments, carriers may hold one or more other payloads and rewritable displays may display status information about the one or more payloads in the carriers. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
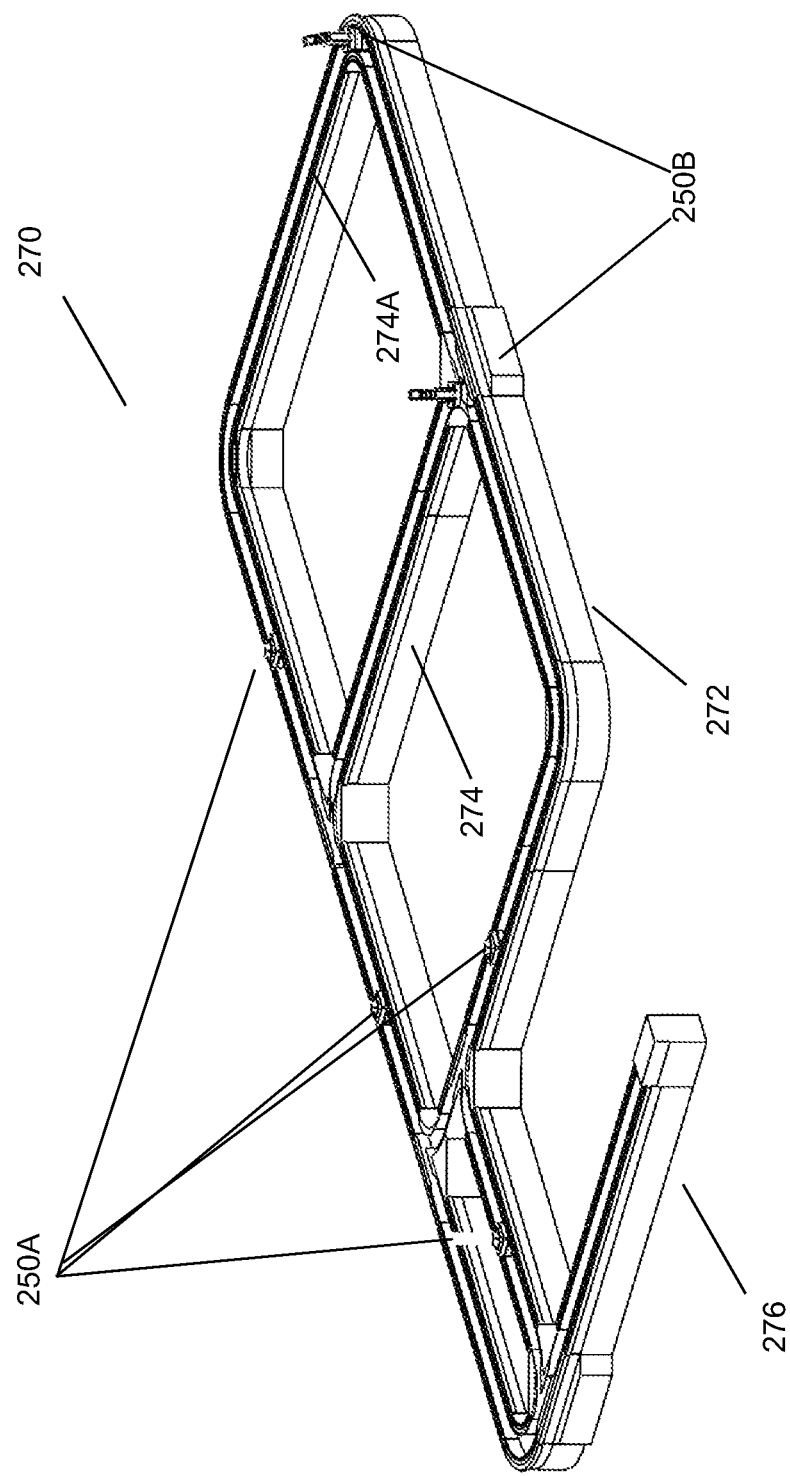
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
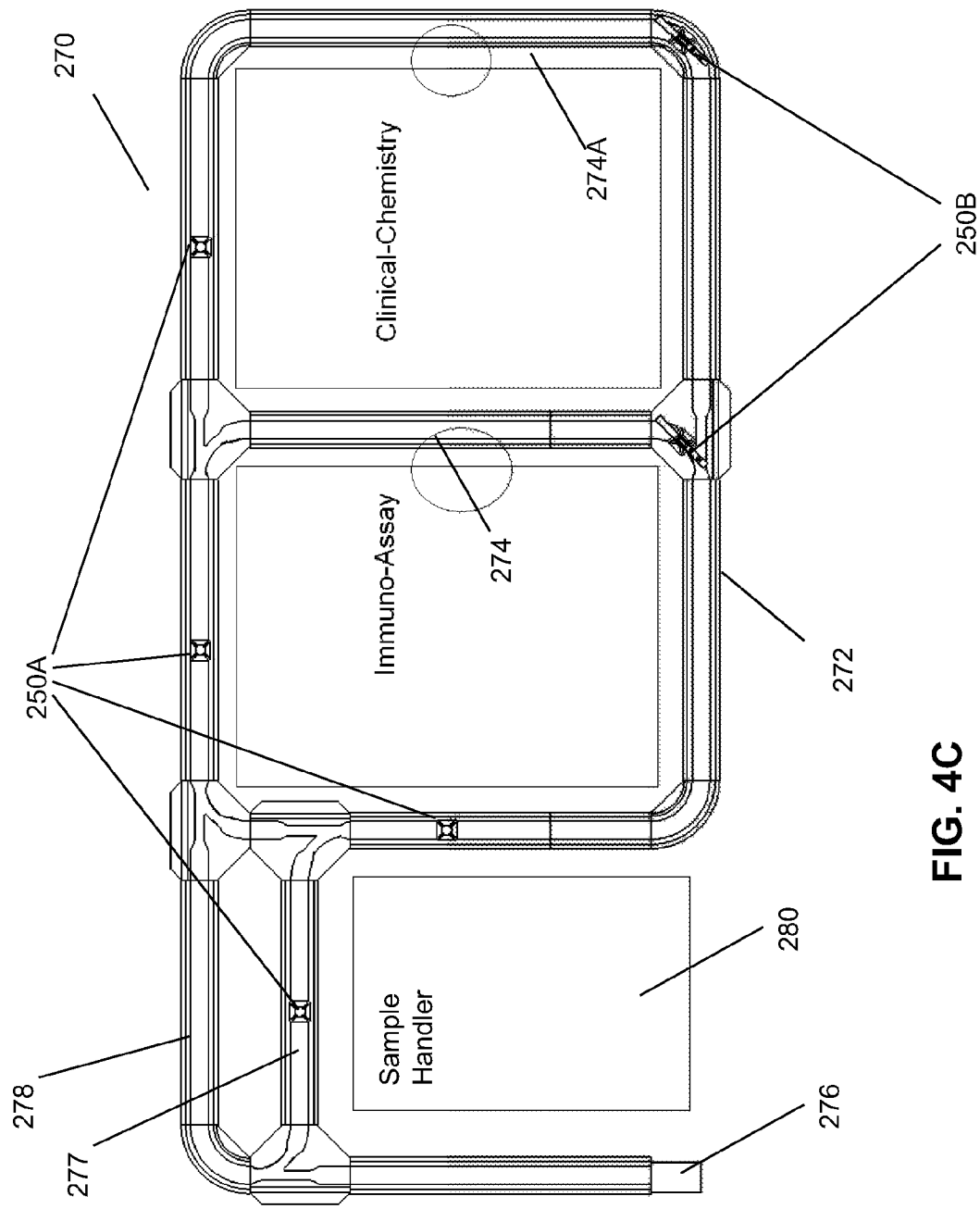
FIG. 4C is a top view of an exemplary automation systems carrier that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Some embodiments of the present invention can utilize intelligent carriers to enable certain improvements over passive pucks on the friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has a priori knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
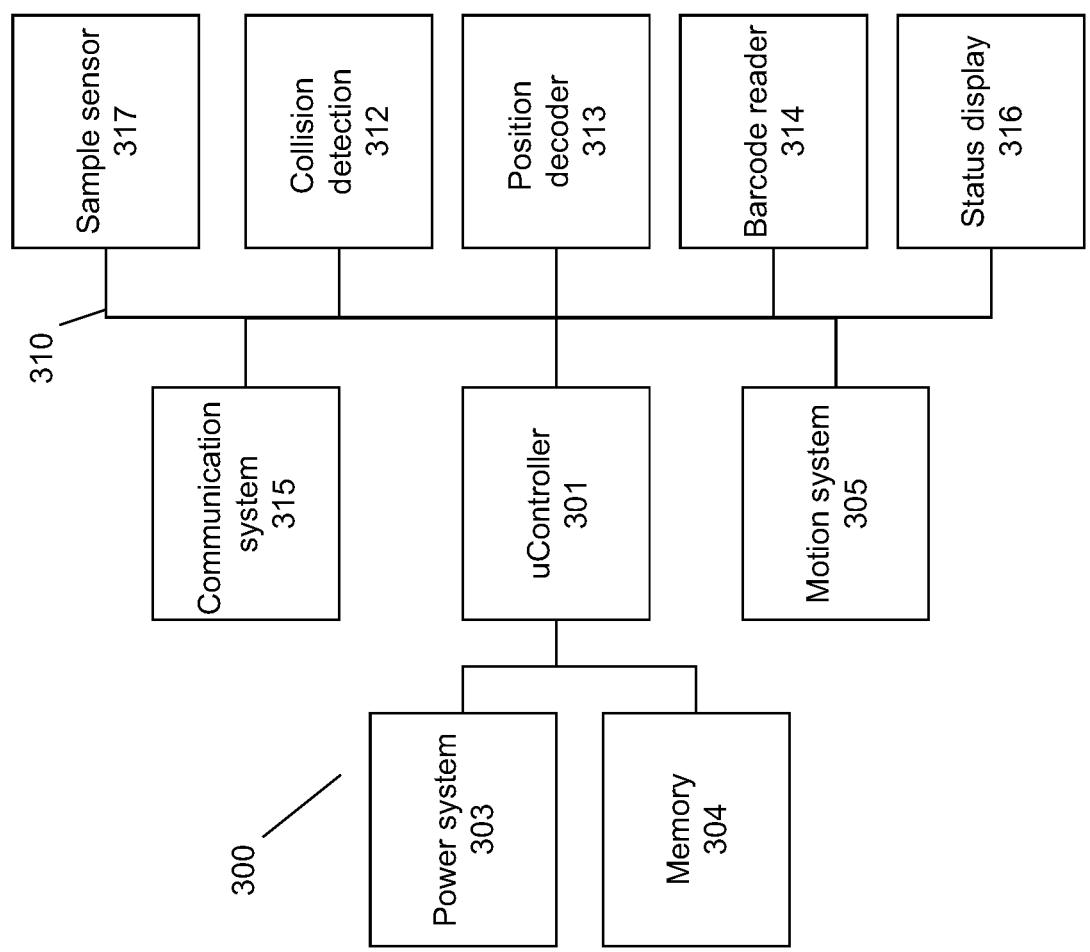
FIG. 5 is a system block diagram of the control systems including onboard active carriers that can be used with certain embodiments disclosed herein.

FIG. 5 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as a bi-stable display (e.g., a cholesteric LCD panel or E-ink display). In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Displaying Status Information

A typical operation in an IVD environment begins with receiving a group of fluid samples to be tested. Each tube has a barcode and the tubes are placed into a rack for transporting. An operator then either hand sorts the tubes, or uses an automation device that sorts the tubes for the operator. In the prior art, these tubes would be organized, but an operator carrying a rack of tubes would have little information about, or little ability to determine, the character of each sample. For example, STAT samples may be placed in an input lane of the track system. These samples are deemed important and should be given priority by the operator when handling samples. However, without the ability to tell at a glance which samples are STAT samples, it may be difficult for an operator to handle STAT samples appropriately. Furthermore, not all samples in a rack which has not yet been placed on an automation track may need to go to the same analyzer. This may cause confusion and slow down the process as an operator carries a tray of samples between multiple machines and attempts to select the appropriate samples to be placed into each machine.

Once placed within an analyzer, one or more testing stations interact with each sample. These stations can determine the current properties of the sample, including detecting whether a sample has problems, such as a low volume or precipitates like clots in a whole blood sample. Some samples may need to go to multiple testing stations and have multiple tests performed upon it. In a typical IVD environment, each sample undergoes around half a dozen tests. In some IVD environments, not all tests are performed by the same analyzer or by stations that are accessible be the same automation system. Therefore, in some embodiments, an operator may need to remove a carrier or tube from an automation system for further processing.

Embodiments of the present invention may solve these issues by providing carriers that include an electronically rewritable surface for automatically displaying status information about a sample. In some embodiments, these carriers can be removed from an automation track and placed into an array or tray for easy transport. The display information can continue to be displayed in the tray and, in some embodiments, may continue to be updated wirelessly while in the tray. In some embodiments, the carriers are designed to display status information while within the track system or within an external tray.

By combining a rewritable surface with intelligent carriers, the carrier has means for automatically updating the status and maintaining and displaying that status. For example, as a carrier moves throughout an automation system, it receives information wirelessly from a controller. This information can include routing information as well as status information about the sample being carried. The status information can then be displayed in a rewritable electronic display using the onboard power memory and control available in the carrier.

The rewritable status display can include a top surface of the carrier. The display may be an active bi-stable display, such as a cholesteric LCD or and E-ink display. Other embodiments include LEDs, electro florescent displays, AMOLEDs, or any other type of display used in portable or mobile devices. These displays may be volatile, such as LCDs, or nonvolatile, such as E-ink displays. By using a nonvolatile display, the display can continue to display status information after it has been updated without applying power to the display. A bi-stable may act as a non-volatile display, maintaining display state with little or no supplied power.

In some embodiments, a bi-stable display is used with a passive carrier, such as a puck. In these embodiments, an external electric field can be applied to the surface of the puck to imprint status information, which will continue to be displayed until rewritten with an electric field. The application of this electric field to the display can be via a planar surface that emits an electric field in a predefined pattern that conveys the status. By placing the display within close proximity to this electric field and the resulting pattern, the display is updated as if it has been electronically stamped. In other embodiments, any display can include pixels or other pattern elements within the display, each served by separate top and/or bottom electrodes. By temporarily applying power to these electrodes, such as by temporary electrical contact, the display can be updated via brief contact and the status information maintained after the contact is broken. It should therefore be understood that embodiments of the present invention are suitable for use with passive devices as well as the active carriers described herein.

Figure 6B:
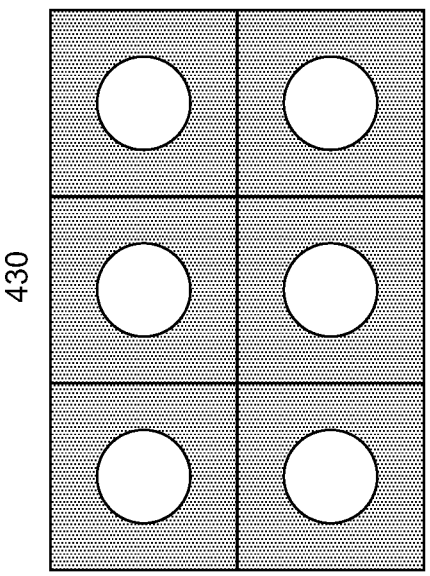
FIG. 6B is a diagrammatic view of multiple exemplary electronically rewritable surfaces for displaying status information on a carrier.
Figure 6A:
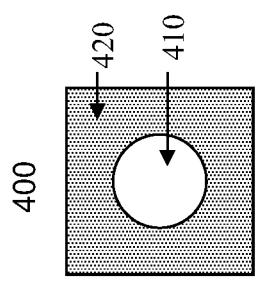
FIG. 6A is a diagrammatic view of an exemplary electronically rewritable surface for displaying status information on a carrier.

FIG. 6A shows an exemplary rewritable display 400. Rewritable display 400 is shown as the top of the carrier, but other configurations are contemplated. Rewritable display 400 includes a hollow area 410 that can be used to accept a sample tube and an electronically rewritable surface 420. Rewritable surface 420 can be an LCD panel, E-ink panel, or any other suitable electronic rewritable surface. In some embodiments, the rewritable display can be a portion of the rewritable surface 420.

As shown in FIG. 6B, multiple carriers can be placed in an array 430, such as when placed in a tray for easy handling by an operator. For example, after samples are sorted by a sorter or an operator, carriers containing samples can be placed in array 430 and information about the status of each sample in the array 430 can be displayed in the surfaces of the rewritable displays of each carrier.

Information can be conveyed via the rewritable surface in several ways, depending on the capabilities of the display surface used. First, color can be used to convey status information. For example, green can show that a sample has completed processing or has successfully passed a quality test. Yellow may show that a sample is still awaiting further testing. Red may show that the sample has an error, such as that foreign bodies have been detected, that the sample is too low on volume to be further tested, etc. STAT samples can also include their own color, such as blue, so that they are readily identifiable next to normal priority samples.

Second, a pattern can be used to convey information. For example, shapes such as diamonds, triangles, squares, circles, logos, textures, or other symbols that are easily differentiated can be displayed on the surface to indicate information about status to an operator. The pattern displayed can also be time varying—a blinking pattern or color can indicate importance of the sample, such as an error. Third, text can be displayed on the surface of the carrier to indicate specific information to an operator, such as the next destination, or the identity of a sample. This text can be helpful in identifying specific samples that an operator is looking for, without the need to scan each barcode since the text is human readable.

Figure 7:
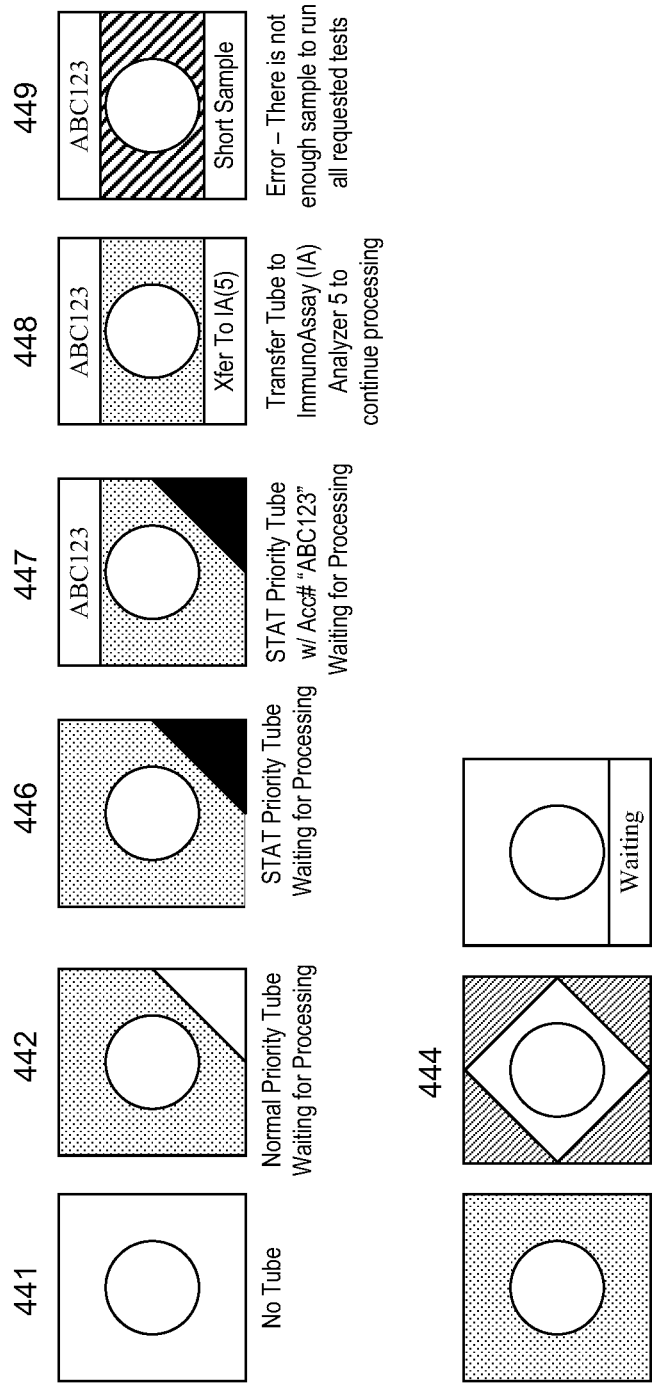
FIG. 7 is a diagrammatic view of multiple exemplary states of electronically rewritable surfaces for displaying status information about a sample.

FIG. 7 shows some exemplary embodiments of visual patterns that can be used to display status information in a rewritable surface of the carrier. Surface 441 shows a blank display, which indicates that a tube is not present or identified. Surface 442 includes a main area whose color or shading indicates the presence of a tube, while a smaller region of the surface is blank indicating the priority (e.g., normal) of the tube. Patterns 444 show exemplary alternative displays for indicating a sample is waiting. These patterns can include a solid shaded or colored surface, a diamond pattern, or text indicating that a sample is waiting. Shading can be accomplished using a digital gray scale value that can be accomplished by partially turning on/off portions of the display (e.g., pixels or regions) or by pulse width modulation of these portions.

Surface 446 includes a main area whose color or shading indicates the presence of a tube, while a smaller region of the surface is solid or colored red, indicating the priority (e.g., STAT) of the tube. Surface 447 shows an alternate embodiment for displaying a STAT sample, including the use of a text field that identifies the sample. Surface 448 shows an example of an embodiment of the surface for indicating that a sample is waiting to be transferred to a specific analyzer or testing station. This includes a text field for displaying the identity of the sample and another text field for identifying the intended destination of the sample, or instructions for the operator to follow. By using instructions, an operator can easily determine what to do with a sample with minimal or no training.

Surface 449 shows an exemplary embodiment for displaying an error. A main area displays an error color (e.g., red) or pattern (e.g., striped, blinking, etc.), while a first text field displays the identity of the sample and a second text field displays the nature of the error, such as indicating the sample is low on volume (e.g., "short sample").

Embodiments can include a text field that includes the identity of the sample. This identity can be the unique identifier in the barcode of the sample or any other indicator of identity, including an ID that is only used in the IVD environment or sample type, patient name, or a record identifier.

FIG. 8 shows an exemplary array of carriers that display the status of multiple samples. In this example, carriers 452, 454, 456 indicate completed samples. A main area includes a first color or pattern, such as green or white that indicates the completed state of the sample. A first text field indicates the identity of each sample, while a second text field indicates the completed status of the sample. Carriers 462, 464, and 466 indicate that testing is pending on those samples. A main area includes a first color or pattern, such as gray or yellow to indicate this pending status. A first text field indicates the identity of each sample, while a second text field indicates instructions to the operator or the next step that an automation system will execute to complete the testing on the sample. Carriers 472, 474, and 476 indicate the presence of an erroneous sample. A main area includes a first color pattern, such as red or black that indicates the error state of the sample. Meanwhile, a first text field indicates the identity of the sample (if known), while a second text field indicates the specific nature of the error. For example, carrier 472 indicates that there is a barcode error with a sample so that its identity cannot be ascertained. Carrier 474 indicates that the volume of sample is insufficient for further testing. Carrier 476 indicates the presence of a clot the sample.

Figure 9:
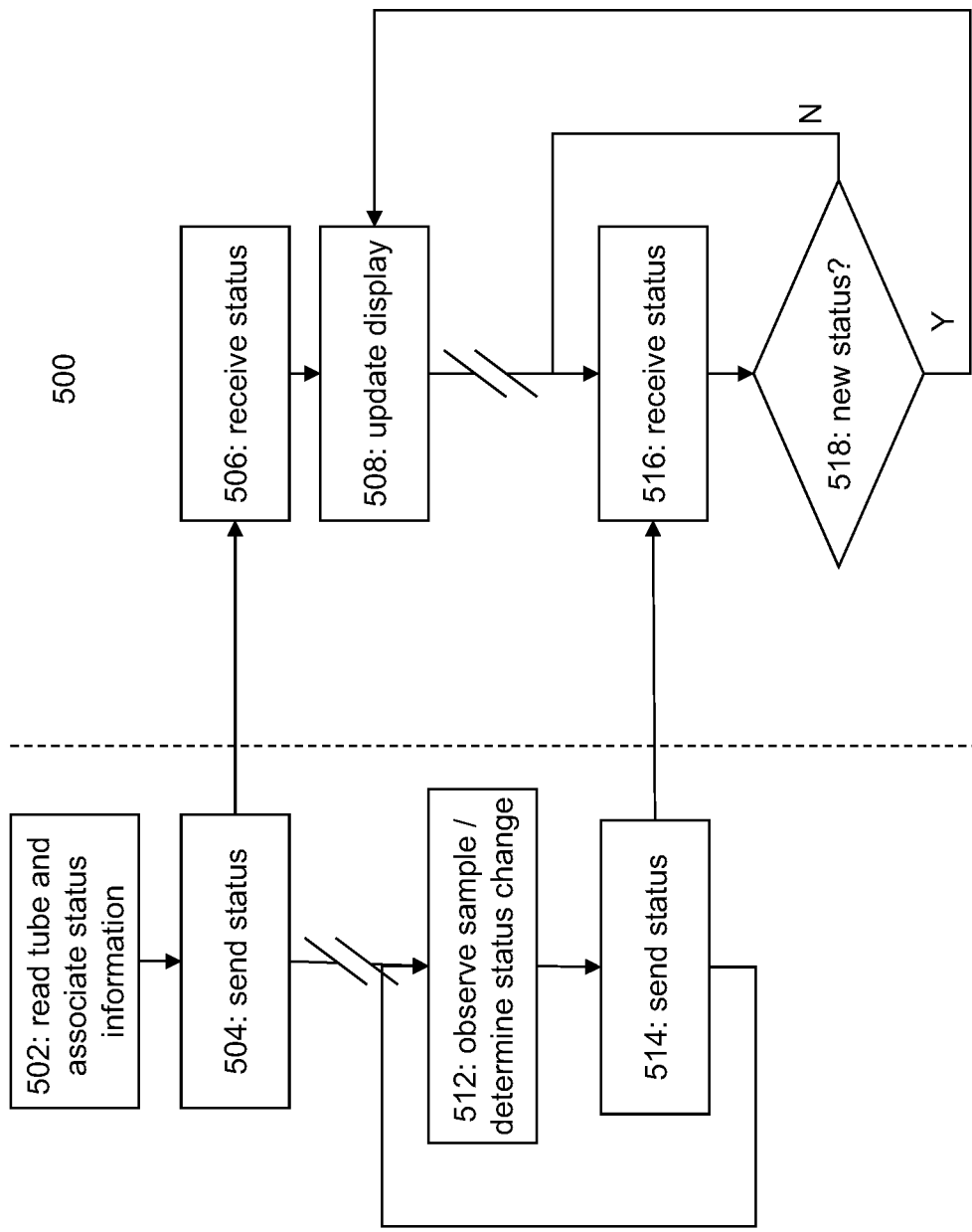
FIG. 9 is a flowchart showing an exemplary operation of an embodiment of an electronically rewriteable status display.

FIG. 9 shows a flowchart of the basic operation 500 of the rewritable display. At step 502, the system reads information about one or more payloads, such as a sample tube, and associates it with a carrier. This can include, for example, scanning of a barcode either automatically or by hand to determine an identity of the sample tube. It can also include using onboard sensors of the carrier to detect the presence of the tube and the presence of a new tube in the carrier after the barcode has been read to determine that the new tube has been placed in the carrier. In some embodiments, step 502 is performed at a system level and the status information of the tube is maintained by a central processor in an automation system. At step 504, the status is communicated to the carrier. In some embodiments, this communication is via wireless communication.

At step 506, the carrier receives status information from the central processor and stores this information in onboard memory. At step 508, the carrier updates the rewritable display panel to indicate the current status. As the carrier moves the sample throughout the automation system, and testing stations interact with the sample, the status can change. At step 512, the automation system observes the sample and determines if the status has changed. This can occur, for example, when a sample pipette interacts with the sample to detect the volume and quality of the sample. This information can be used to determine a status (e.g., an error) of the sample. Furthermore, once a testing station completes a test on the sample, the status of the sample (such as next test, pending/complete, etc.) will change. At step 514, the updated status is sent to the carrier wirelessly.

At step 516, the carrier receives the new status from the automation system via the wireless transceiver. At step 518, the carrier determines if the status is now different than that being displayed. If not, the carrier continues to wait for further updates to the status of the sample. If the status has changed and the display should be updated, the carrier then updates the display at step 508.

In some embodiments, an operator receives a rack of tubes for testing. These tubes are not yet placed into carriers. An operator will scan the barcodes of each so that the automation system knows the identity and other information, such as the scheduled tests for the sample. A central processor for the automation system will then assign the tube to a specific carrier. The central processor can then communicate this relationship to that carrier, causing the assigned carrier to blink or light up. This allows the operator to determine which carrier the tube has been assigned to, and place the tube in the proper carrier.

In some embodiments, after a tube has been scanned by an operator, the central processor will begin polling carriers in the area and identify which carriers receive a new tube within a short period of time after the tube has been scanned. In this way, the central scheduler can automatically identify the carrier into which the operator has placed the tube. Once the identity of the carrier is known, the central processor can communicate status information about the tube/sample, such as identity, to the appropriate carrier. This can be used to ensure reliable chain of custody for samples.

The status display can also be used, in some embodiments, to indicate whether a sample in a carrier meets certain operator-defined criteria. For example, an operator may want to determine which samples are associated with a certain patient. The operator can submit a query to the central controller that communicates status information to the carriers. The controller can determine which samples match the query by comparing the query to a database of status information of the samples in the IVD environment. This can be maintained by the central controller. In response to the query, the central controller can then update the status information of the responsive carriers such that they can temporarily display their inclusion in a responsive group of carriers. For example, the central controller can send instructions wirelessly to all carriers of samples of the requested patient to cause their displays to blink, so that an operator can tell at a glance which samples are responsive to the query.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning), a carrier returns to step 504 to determine its next trajectory.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A carrier for use in an in vitro diagnostics environment comprising:
   a bracket for accepting one or more patient sample tubes; and
   at least one surface of the carrier having an electronically rewritable display, the at least one surface including an opening to receive the one or more patient sample tubes,
   wherein the carrier automatically updates the electronically rewritable display to provide a visual indication of status information regarding the status of the one or more patient sample tubes, where the status information is displayed in addition to any barcode label affixed to the one or more patient sample tubes.

2. The carrier of claim 1, wherein the status information can be updated wirelessly by a central controller.

3. The carrier of claim 1, wherein the electronically rewritable display is a bi-stable display.

4. The carrier of claim 1, wherein the display can be updated by temporary application of power to electrical contacts on the carrier.

5. The carrier of claim 1, wherein the electronically rewritable display is a non-volatile display.

6. The carrier of claim 1, wherein the status information is conveyed by displaying a color on at least a portion of the electronically rewritable display.

7. The carrier of claim 1, wherein the status information is conveyed by displaying a pattern on at least a portion of the electronically rewritable display.

8. The carrier of claim 7, wherein the pattern comprises a blinking pattern.

9. The carrier of claim 1, wherein the status information is conveyed by displaying text on at least a portion of electronically rewritable display.

10. The carrier of claim 9, wherein the text comprises instructions for the handling of the one or more patient sample tubes.

11. The carrier of claim 1, wherein the status information indicates a priority of the one or more patient sample tubes.

12. The carrier of claim 1, wherein the status information indicates an identity of at least one patient sample among the one or more patient sample tubes.

13. The carrier of claim 1, wherein the status information indicates a response to a query by an operator.

14. The carrier of claim 13, wherein at least a portion of the rewritable electronic display is made to appear different from a group of other carriers in response to the query.

15. The carrier of claim 1, wherein the rewritable electronic display comprises more than one region for displaying the status information.

16. The carrier of claim 1, wherein the carrier comprises one or more sensors for determining the presence of the one or more patient sample tubes.

17. A method for displaying status information of one or more patient sample tubes being transported in an in vitro diagnostics environment comprising the steps of:
   determining the identity of the one of more patient sample tubes from identifying information affixed to the one or more patient sample tubes;
   associating information pertaining to the one or more patient sample tubes with a carrier holding the one or more patient sample tubes;
   receiving, by the carrier, status information pertaining to the one or more patient sample tubes; and
   displaying the status information on an electronically rewritable surface of the carrier, the surface being configured receive the one or more patient sample tubes.

18. The method of claim 17, further comprising the step of updating the electronically rewritable display to reflect one or more changes in the status information of the one or more patient sample tubes.

19. The method of claim 18, wherein the one or more changes comprises an error condition pertaining to the one or more patient sample tubes.

20. The method of claim 17, wherein the step of associating information pertaining to the one or more patient sample tubes comprises reading a barcode on the one or more payloads to determine an identity of the patient sample tubes.

21. The method of claim 20, wherein the step of associating information pertaining to the one or more patient sample tubes further comprises changing the display of the carrier to distinguish the carrier from a group of carriers and to instruct the operator to place the one or more patient sample tubes into the carrier.

22. The method of claim 20, wherein the step of associating information pertaining to the one or more patient sample tubes further comprises detecting the presence of a new patient sample tube in the carrier after the barcode has been read to determine that the new patient sample tube has been placed in the carrier.

23. The method of claim 17, further comprising the step of updating the electronically rewritable display to reflect the result of a query if the one or more patient sample tubes meets a criteria of the query.

24. A carrier for use in an in vitro diagnostics environment comprising:
   an electronically rewriteable display configured to display status information, the electronically rewriteable display being disposed on at least one surface of the carrier that is configured to receive one or more patient sample tubes;
   a processor configured to update the electronically rewriteable display; and
   a wireless receiver configured to receive the status information for display, wherein the status information relates to the status of the one or more one or more patient sample tubes being carried by the carrier and is displayed in addition to any barcode label affixed to the one or more patient sample tubes.

25. The carrier of claim 24, wherein the electronically rewritable display is an electronic ink display.

26. The carrier of claim 24, wherein the display can be updated by temporary application of power to electrical contacts on the carrier.

27. The carrier of claim 24, wherein the electronically rewritable display is a non-volatile display.

28. The carrier of claim 24, wherein the status information is conveyed by displaying a color on at least a portion of the electronically rewritable display.

29. The carrier of claim 24, wherein the status information is conveyed by displaying a pattern on at least a portion of the electronically rewritable display.

30. The carrier of claim 29, wherein the pattern comprises a blinking pattern.

31. The carrier of claim 24, wherein the status information is conveyed by displaying text on at least a portion of electronically rewritable display.

32. The carrier of claim 31, wherein the text comprises instructions for the handling of the one or more patient sample tubes.

33. The carrier of claim 24, wherein the status information indicates a priority of the one or more patient sample tubes.

34. The carrier of claim 24, wherein the status information indicates an identity of at least one patient sample among the one or more patient sample tubes.

35. The carrier of claim 24, wherein the status information indicates a response to a query by an operator.

36. The carrier of claim 35, wherein at least a portion of the rewritable electronic display is made to appear different from a group of other carriers in response to the query.

37. The carrier of claim 24, wherein the rewritable electronic display comprises more than one region for displaying the status information.

38. The carrier of claim 24, wherein the carrier comprises one or more sensors for determining the presence of the one or more patient sample tubes.

* * * * *